US009888963B2

(12) United States Patent
Brannan et al.

(10) Patent No.: US 9,888,963 B2
(45) Date of Patent: Feb. 13, 2018

(54) ELECTROSURGICAL DEVICES WITH BALUN STRUCTURE FOR AIR EXPOSURE OF ANTENNA RADIATING SECTION AND METHOD OF DIRECTING ENERGY TO TISSUE USING SAME

(71) Applicant: COVIDIEN LP, Mansfield, MA (US)

(72) Inventors: Joseph D. Brannan, Lyons, CO (US); Joseph A. Paulus, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/451,694

(22) Filed: Mar. 7, 2017

(65) Prior Publication Data

US 2017/0172656 A1    Jun. 22, 2017

Related U.S. Application Data

(63) Continuation of application No. 14/690,912, filed on Apr. 20, 2015, now Pat. No. 9,603,662, which is a
(Continued)

(51) Int. Cl.
*A61B 18/18*    (2006.01)
*A61B 18/00*    (2006.01)

(52) U.S. Cl.
CPC ............ *A61B 18/1815* (2013.01); *A61B 2018/00023* (2013.01); *A61B 2018/00577* (2013.01);
(Continued)

(58) Field of Classification Search
CPC . A61B 18/18; A61B 18/1815; A61B 18/1206; A61B 2018/00023;
(Continued)

(56) References Cited

U.S. PATENT DOCUMENTS

D263,020 S    2/1982  Rau, III
4,534,347 A   8/1985  Taylor
(Continued)

FOREIGN PATENT DOCUMENTS

CN    1103807 C    3/2003
DE     390937 C    3/1924
(Continued)

OTHER PUBLICATIONS

European Search Report EP 08019920.1 dated Mar. 27, 2009.
(Continued)

*Primary Examiner* — Michael Peffley
*Assistant Examiner* — Khadijeh Vahdat

(57) ABSTRACT

An energy applicator for directing energy to tissue includes a feedline having an inner conductor, an outer conductor and a dielectric material disposed therebetween, and an antenna assembly having a radiating section operably coupled to the feedline. The energy applicator also includes a first balun structure configured to substantially confine energy to the radiating section when the energy applicator is energized and disposed in tissue, and a second balun structure configured to substantially prevent energy emitted from the radiating section from propagating proximal to the second balun structure along the feedline when the energy applicator is energized but not disposed in tissue.

10 Claims, 11 Drawing Sheets

Related U.S. Application Data continuation of application No. 12/777,984, filed on May 11, 2010, now Pat. No. 9,561,076.

(52) U.S. Cl.
CPC ............... *A61B 2018/1869* (2013.01); *A61B 2018/1892* (2013.01)

(58) Field of Classification Search
CPC .......... A61B 2018/00589; A61B 2018/00601; A61B 2018/00642; A61B 2018/00702; A61B 2018/1286; A61B 2018/1838; A61B 2018/1869; A61B 2018/1892
USPC .................................................. 606/33–50
See application file for complete search history.

(56) References Cited

U.S. PATENT DOCUMENTS

| | | |
|---|---|---|
| 4,583,589 A | 4/1986 | Kasevich |
| D295,893 S | 5/1988 | Sharkany et al. |
| D295,894 S | 5/1988 | Sharkany et al. |
| 5,026,959 A | 6/1991 | Ito et al. |
| 5,056,106 A | 10/1991 | Wang et al. |
| 5,057,106 A | 10/1991 | Kasevich et al. |
| 5,301,687 A | 4/1994 | Wong et al. |
| 6,016,452 A | 1/2000 | Kasevich |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| 6,398,781 B1 | 6/2002 | Goble et al. |
| 6,485,486 B1 | 11/2002 | Trembly et al. |
| 6,706,040 B2 | 3/2004 | Mahon et al. |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| 7,318,824 B2 | 1/2008 | Prakash et al. |
| D564,662 S | 3/2008 | Moses et al. |
| 7,527,623 B2 | 5/2009 | Prakash et al. |
| 7,594,313 B2 | 9/2009 | Prakash et al. |
| D613,412 S | 4/2010 | DeCarlo |
| 8,188,435 B2 | 5/2012 | Podhajsky et al. |
| 8,313,486 B2 | 11/2012 | Kim et al. |
| 8,409,188 B2 | 4/2013 | Kim et al. |
| 8,491,579 B2 | 7/2013 | Rossetto |
| 8,568,404 B2 | 10/2013 | Brannan |
| 8,617,153 B2 | 12/2013 | Lee et al. |
| 8,652,127 B2 | 2/2014 | Prakash et al. |
| 8,672,923 B2 | 3/2014 | Ladtkow et al. |
| 8,672,933 B2 | 3/2014 | Shiu et al. |
| 8,764,744 B2 | 7/2014 | Brannan |
| 8,777,939 B2 | 7/2014 | Lee et al. |
| 9,561,076 B2 | 2/2017 | Brannan et al. |
| 9,603,662 B2 | 3/2017 | Brannan et al. |
| 2002/0022836 A1 | 2/2002 | Goble et al. |
| 2003/0088242 A1* | 5/2003 | Prakash ............... A61B 18/18 606/33 |
| 2003/0097064 A1* | 5/2003 | Talpade ............... A61B 5/055 600/434 |
| 2005/0085881 A1 | 4/2005 | Prakash et al. |
| 2006/0155270 A1 | 7/2006 | Hancock et al. |
| 2006/0282069 A1 | 12/2006 | Prakash et al. |
| 2007/0106332 A1* | 5/2007 | Denker ............... A61N 1/375 607/2 |
| 2009/0005766 A1 | 1/2009 | Brannan |
| 2009/0187180 A1 | 7/2009 | Brannan |
| 2009/0295674 A1 | 12/2009 | Bonn |
| 2010/0045559 A1 | 2/2010 | Rossetto |
| 2010/0053015 A1* | 3/2010 | Willyard ............... A61B 18/18 343/790 |
| 2010/0082082 A1 | 4/2010 | Prakash et al. |
| 2010/0097284 A1 | 4/2010 | Brannan et al. |
| 2011/0190754 A1 | 8/2011 | Kim et al. |
| 2011/0208177 A1* | 8/2011 | Brannan ............ A61B 18/1815 606/33 |
| 2011/0208180 A1 | 8/2011 | Brannan |
| 2011/0213353 A1 | 9/2011 | Lee et al. |
| 2011/0238053 A1 | 9/2011 | Brannan et al. |
| 2011/0238055 A1 | 9/2011 | Kim et al. |
| 2011/0270240 A1 | 11/2011 | Shiu et al. |
| 2011/0282336 A1 | 11/2011 | Brannan et al. |
| 2011/0295245 A1 | 12/2011 | Willyard et al. |
| 2011/0299719 A1 | 12/2011 | Podhajsky et al. |
| 2011/0301589 A1 | 12/2011 | Podhajsky et al. |
| 2011/0301590 A1 | 12/2011 | Podhajsky et al. |
| 2011/0301591 A1 | 12/2011 | Podhajsky et al. |
| 2011/0319880 A1 | 12/2011 | Prakash et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 246350 A1 | 11/1987 |
| EP | 0521264 A2 | 1/1993 |
| EP | 556705 A1 | 8/1993 |
| EP | 0558429 A1 | 9/1993 |
| EP | 836868 A2 | 4/1998 |
| EP | 882955 A1 | 12/1998 |
| EP | 1159926 A3 | 3/2003 |
| EP | 2008604 A2 | 12/2008 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |

(56) References Cited

FOREIGN PATENT DOCUMENTS

| | | |
|---|---|---|
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | S6049803 A | 3/1985 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 200129356 | 2/2001 |
| JP | 2001128990 A | 5/2001 |
| JP | 2001231870 A | 8/2001 |
| JP | 2001521311 A | 11/2001 |
| JP | 2002541884 A | 12/2002 |
| JP | 2004518471 A | 6/2004 |
| JP | 2006507865 A | 3/2006 |
| JP | 2008142467 A | 6/2008 |
| JP | 2009006150 A | 1/2009 |
| JP | 2009027516 A | 2/2009 |
| SU | 166452 | 1/1965 |
| SU | 401367 A1 | 10/1973 |
| SU | 727201 A2 | 4/1980 |
| WO | 03039385 A2 | 5/2003 |
| WO | 2003/047043 A1 | 6/2003 |
| WO | 2004047659 A2 | 6/2004 |
| WO | 2009094422 A1 | 7/2009 |
| WO | 2010035831 A1 | 4/2010 |

OTHER PUBLICATIONS

European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/U504/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/423,609, filed Apr. 14, 2009.
U.S. Appl. No. 12/436,231, filed May 6, 2009.
U.S. Appl. No. 12/436,237, filed May 6, 2009.
U.S. Appl. No. 12/436,239, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.

(56) References Cited

OTHER PUBLICATIONS

Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.-Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
Roy W. Lewallen "Baluns: What They Do and How They Do It" ARRL Antenna Compendium, vol. 1 , copyright 1985, by the American Radio Relay League, Inc. pp. 157-164.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et at., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N. J., 1970.
Kennedy et al., "High-burst-strength, feedback-controlled bipolar vessel sealing" Surgical Endoscopy (1998) 12: 876-878.
European Communication dated Mar. 14, 2017, corresponding to European Application No. 11 003 822.1; 7 pages.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.

(56) References Cited

OTHER PUBLICATIONS

European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/556,238, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,323, filed Nov. 16, 2009.
U.S. Appl. No. 12/619,462, filed Nov. 16, 2009.
U.S. Appl. No. 12/620,289, filed Nov. 17, 2009.
U.S. Appl. No. 12/642,623, filed Dec. 18, 2009.
U.S. Appl. No. 12/686,726, filed Jan. 13, 2010.
U.S. Appl. No. 12/761,267, filed Apr. 15, 2010.
U.S. Appl. No. 12/769,457, filed Apr. 28, 2010.
U.S. Appl. No. 12/819,330, filed Jun. 21, 2010.
International Search Report EP11003822 dated Aug. 4, 2011.
Partial European Search Report for European Patent Appln. No. 11003822.1 dated Aug. 4, 2011, (5 pages).
U.S. Appl. No. 08/136,098; Oct. 14, 1993; Roger A. Stern.
U.S. Appl. No. 08/483,742; Jun. 7, 1995; Roger A. Stern.
Extended European Search Report dated Nov. 25, 2011, corresponding to European Application No. 11003822.1; 10 pages.
Japanese Notice of Reasons for Rejection (with English Translation), dated Oct. 7, 2014, corresponding to Japanese Patent Application No. 2011-100326; 8 total pages.
Japanese Notice of Reasons for Rejection (with English Translation), dated Mar. 31, 2015, corresponding to Japanese Patent Application No. 2011-100326; 4 total pages.
Japanese Office Action (with English translation), dated Jul. 12, 2016, corresponding to Japanese Application No. 2015-126524; 4 total pages.
Japanese Office Action (with English translation), dated Jul. 12, 2016, corresponding to Japanese Application No. 2015-126524; 4 total page.

* cited by examiner

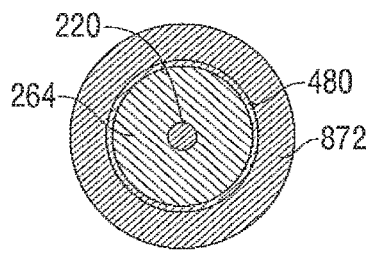
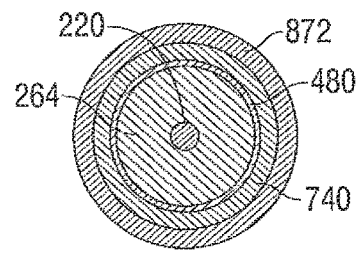
FIG. 19A  FIG. 19B
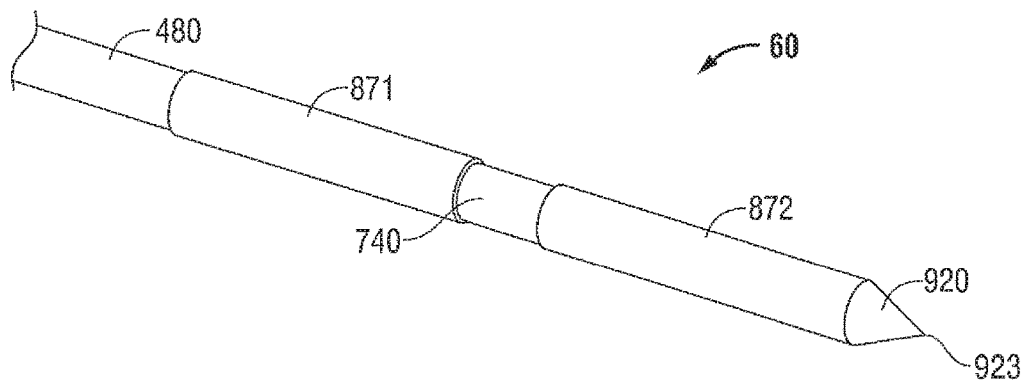
FIG. 20
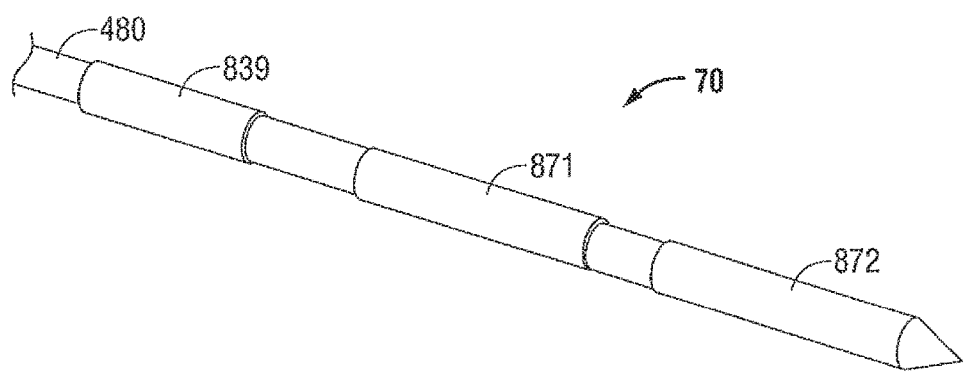
FIG. 21

ELECTROSURGICAL DEVICES WITH BALUN STRUCTURE FOR AIR EXPOSURE OF ANTENNA RADIATING SECTION AND METHOD OF DIRECTING ENERGY TO TISSUE USING SAME

CROSS-REFERENCE TO RELATED APPLICATIONS

This application is a continuation of U.S. patent application Ser. No. 14/690,912, filed on Apr. 20, 2015, which is a continuation application of U.S. patent application Ser. No. 12/777,984, filed on May 11, 2010 (now U.S. Pat. No. 9,561,076), the entire contents of each of which are incorporated by reference herein.

BACKGROUND

1. Technical Field

The present disclosure relates to electrosurgical devices suitable for use in tissue ablation applications and, more particularly, to electrosurgical devices with a balun structure for air exposure of an antenna radiating section and method of directing energy to tissue using the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

A microwave transmission line typically includes a long, thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, such as a length of transmission line or coaxial cable, is provided with a plurality of openings through which energy "leaks" or radiates away from the guiding structure. This type of construction is typically referred to as a "leaky coaxial" or "leaky wave" antenna. The design of the microwave probe radiating antenna influences the thermal distribution.

Some ablation targeted lesions are too small or too hard to be punctured by an ablation probe. In these cases, doctors may place the probe as close as possible to the lesion and perform an ablation. With non-directional ablation probes, the ablation may radiate to both sides of the probe.

Treatment of certain tumors may involve probe repositioning during the ablation procedure, such as where the tumor is larger than the probe or has a shape that does not correspond with available probe geometry or radiation pattern. The surgeon, before or after treatment is completed, may remove the probe from tissue while power is delivered to the probe antenna and energy, e.g., radiant energy, such as heat, and/or electromagnetic radiation, may be transmitted along the shaft of the probe toward the surgeon's hand.

SUMMARY

The present disclosure relates to an energy applicator for directing electromagnetic energy to tissue including a feedline having an inner conductor, an outer conductor and a dielectric material disposed therebetween, and an antenna assembly having a radiating section operably coupled to the feedline. The energy applicator also includes a first balun structure configured to substantially confine electromagnetic energy to the radiating section when the energy applicator is energized and disposed in tissue, and a second balun structure configured to substantially prevent electromagnetic energy emitted from the radiating section from propagating proximal to the second balun structure along the feedline when the energy applicator is energized but not disposed in tissue.

The present disclosure also relates to a method of directing energy to tissue including the steps of providing an energy applicator, positioning the energy applicator to tissue, and transmitting energy from an energy source through the radiating section to tissue. The energy applicator includes a feedline, an antenna assembly having a radiating section operably coupled to the feedline, a first balun configured to substantially confine electromagnetic energy to the radiating section, and a second balun configured to substantially prevent electromagnetic energy emitted from the radiating section from propagating proximal to the second balun along the feedline when the energy applicator is energized but not inserted in tissue.

BRIEF DESCRIPTION OF THE DRAWINGS

Objects and features of the presently disclosed energy applicators will become apparent to those of ordinary skill in the art when descriptions of various embodiments thereof are read with reference to the accompanying drawings, of which:

FIG. 19A is a cross-sectional view of a distal portion of the energy applicator of FIG. 18 according to an embodiment of the present disclosure;

FIG. 19B is a cross-sectional view of another distal portion of the energy applicator of FIG. 18 according to an embodiment of the present disclosure;

FIG. 20 is a partial, perspective view of the energy applicator of FIG. 18 shown with a tapered portion extending distally of the distal electrically-conductive sleeve member according to an embodiment of the present disclosure;

FIG. 21 is a partial, perspective view of the energy applicator of FIG. 20 shown with a radiating section air-exposure balun according to an embodiment of the present disclosure;

DETAILED DESCRIPTION

Figure 1:
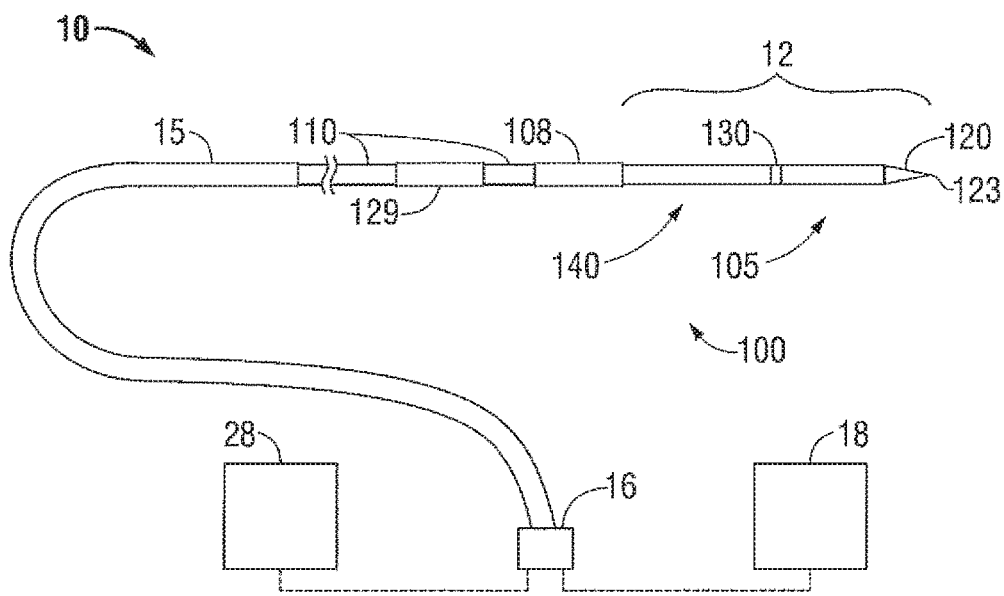
FIG. 1 is a schematic diagram of an ablation system according to an embodiment of the present disclosure.

Hereinafter, embodiments of the presently disclosed energy applicator with radiating section air-exposure balun structure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as microwave ablation, radio frequency (RF) ablation or microwave ablation assisted resection. As it is used in this description, "transmission line" generally refers to any transmission medium that can be used for the propagation of signals from one point to another.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or submultiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

Various embodiments of the present disclosure provide energy applicators for treating tissue and methods of directing electromagnetic radiation to tissue. Embodiments may be implemented using electromagnetic radiation at microwave frequencies or at other frequencies. An electrosurgical system including an energy applicator with radiating section air-exposure balun, according to various embodiments, is designed and configured to operate between about 300 MHz and about 10 GHz.

Various embodiments of the presently disclosed energy applicators with radiating section air-exposure balun structure are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

Various embodiments of the presently disclosed energy applicators with radiating section air-exposure balun structure may include sequential and/or overlapping balun structures. Sequential baluns may have a relatively short length, and may include high-dielectric materials within the non-conductive layers thereof. In embodiments, the sequential and overlapping balun structures may be designed to be lossless structures.

FIG. 1 shows an electrosurgical system 10 according to an embodiment of the present disclosure that includes an energy applicator (also referred to herein as an electromagnetic energy delivery device) or probe 100. An embodiment of an electromagnetic energy delivery device suitable for use in tissue ablation applications, such as the probe 100 of FIG. 1, in accordance with the present disclosure, is shown in more detail in FIGS. 2 through 4. It will be understood, however, that other probe embodiments (e.g., 103 shown in FIG. 10) may also be used.

Probe 100 generally includes an antenna assembly 12 having a radiating portion (e.g., 50 shown in FIG. 2) connected by a feedline 110 (or shaft) via a transmission line 15 to a connector 16, which may further operably connect the probe 100 to a power generating source 28, e.g., a microwave or RF electrosurgical generator. Probe 100, according to various embodiments, includes a first balun structure 108, having a proximal end 106 and a distal end 107. The shape and size of the antenna assembly 12 and the first balun structure 108 may be varied from the configuration depicted in FIGS. 1 and 2. In operation, microwave energy having a wavelength, lambda ($\lambda$), is transmitted through the antenna assembly 12, e.g., along the radiating portion 50, and radiated into the surrounding medium, e.g., tissue.

Figure 2:
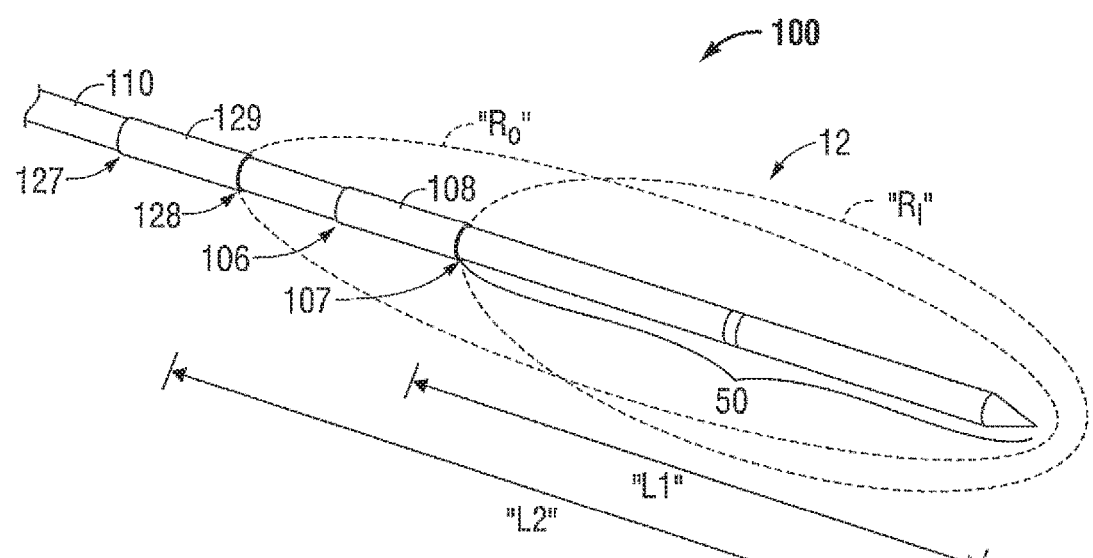
FIG. 2 is a partial, perspective view of an energy applicator according to an embodiment of the present disclosure.

First balun structure 108, which is described in more detail later in this disclosure, generally includes a balun insulator (e.g., 348 shown in FIG. 3) and a balun outer conductor (e.g., 368 shown in FIG. 3) disposed around the outer peripheral surface of the balun insulator, or portions thereof, and may include a balun short (e.g., 378 shown in FIG. 3). First balun structure 108, according to various embodiments, is configured to substantially confine electromagnetic radiation or energy to the radiating section 50 when the probe 100 is energized disposed in tissue. FIG. 2 illustrates a diagrammatic representation of a radiation pattern "$R_f$" of electromagnetic energy emitted by the radiating section 50 when the probe 100 is energized disposed in tissue, showing that energy is emitted distal to the distal end 107 of the first balun structure 108. In some embodiments, the first balun structure 108 may be a quarter-wavelength, ¼ $\lambda$, sleeve balun, or a ¾ $\lambda$ sleeve balun. Odd harmonics (e.g., ¼ $\lambda$, ¾ $\lambda$, etc.) may cause a current null at the balun entrance, which may maintain a desired radiation pattern.

Feedline 110 may be formed from a suitable flexible, semi-rigid or rigid microwave conductive cable, and may connect directly to an electrosurgical power generating source 28. Alternatively, the feedline 110 may electrically connect the antenna assembly 12 via the transmission line 15 to the generator 28. Feedline 110 may have a variable length from a proximal end of the antenna assembly 12 to a distal end of transmission line 15 ranging from a length of about one inch to about twelve inches. Feedline 110 may be formed of suitable electrically-conductive materials, e.g., copper, gold, silver or other conductive metals or metal alloys having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, or decrease energy loss, etc. In some embodiments, the feedline 110 includes stainless steel, and to improve the conductivity thereof, the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor that extends distal of the feedline 110 into the antenna assembly 12. Feedline 110 may be cooled by fluid, e.g., saline or water, to improve power handling, and may include a stainless steel catheter.

In some embodiments, the power generating source 28 is configured to provide microwave energy at an operational frequency from about 300 MHz to about 2500 MHz. In other embodiments, the power generating source 28 is configured to provide microwave energy at an operational frequency from about 300 MHz to about 10 GHz. Power generating source 28 may be configured to provide various frequencies of electromagnetic energy. Transmission line 15 may additionally, or alternatively, provide a conduit (not shown) configured to provide coolant fluid from a coolant source 18 to the probe 100.

Figure 3:
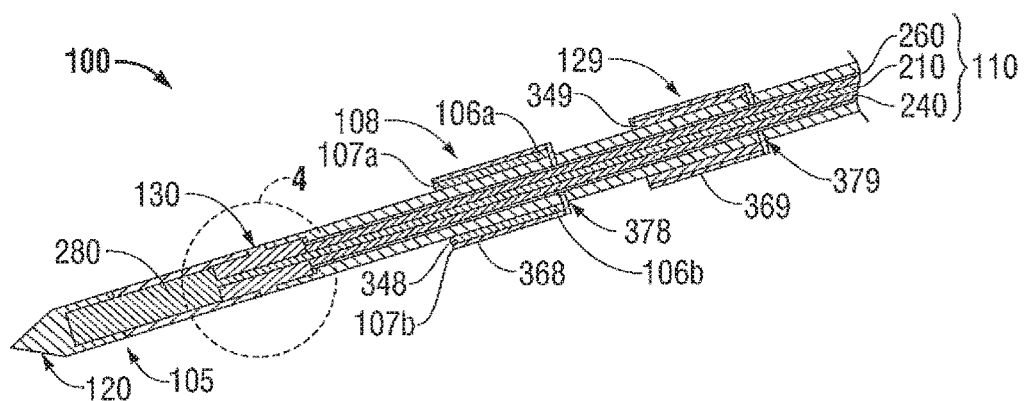
FIG. 3 is a partial, cross-sectional view of the energy applicator of FIG. 2 according to an embodiment of the present disclosure.
Figure 4:
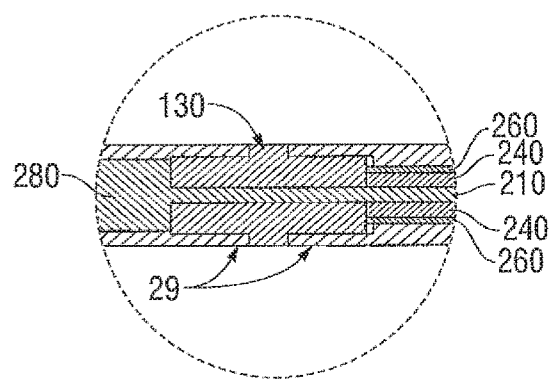
FIG. 4 is an enlarged view of the indicated area of detail of FIG. 3 according to an embodiment of the present disclosure.

Antenna assembly 12 generally includes an inner conductor 210, an outer conductor 260, and may include a first dielectric material 240 separating the inner conductor 210 and the outer conductor 260, for example, as shown in FIGS. 3 and 4. In some embodiments, the inner conductor 210 is formed from a first electrically conductive material (e.g., stainless steel) and the outer conductor 260 is formed from a second electrically conductive material (e.g., copper). In some embodiments, the outer conductor 260 coaxially surrounds the inner conductor 210 along a distal portion of the antenna assembly 12. Inner conductor 210 and the outer conductor 260 may be formed from any suitable electrically conductive material.

First dielectric material 240 may be formed from any suitable dielectric material, including, but not limited to, ceramics, water, mica, polyethylene, polyethylene terephthalate, polyimide, polytetrafluoroethylene (PTFE) (e.g., TEFLON®, manufactured by E. I. du Pont de Nemours and Company of Wilmington, Del., United States), glass, or metal oxides. Antenna assembly 12 may be provided with a second dielectric material 29 surrounding the outer conductor 260 and/or the puck 130, or portions thereof. Second dielectric material 29 may be formed from any suitable dielectric material. In some embodiments, the second dielectric material 29 is formed from a material with a dielectric constant different than the dielectric constant of the first dielectric material 240.

In some embodiments, the antenna assembly 12 includes a conductor end portion 280 that may be formed from any suitable electrically conductive material. In some embodiments, the conductor end portion 280 is coupled to the inner conductor 210 and may be formed of the same material as the inner conductor 210. Tapered region 120, or portions thereof, may surround a proximal portion of the conductor end portion 280. In some embodiments, the conductor end portion 280 is substantially cylindrically shaped, and may be formed from stainless steel. The shape and size of the conductor end portion 280 may be varied from the configuration depicted in FIG. 3. In some embodiments, at least a portion of the conductor end portion 280 is surrounded by the second dielectric material 29.

Located at the distal end of the antenna assembly 12 is an end cap or tapered portion 120, which may terminate in a sharp tip 123 to allow for insertion into tissue with minimal resistance. One example of a straight probe with a sharp tip that may be suitable for use as the energy applicator 100 is commercially available under the trademark EVIDENT™ offered by Covidien. The end cap or tapered portion 120 may include other shapes, such as, for example, a tip 123 that is rounded, flat, square, hexagonal, or cylindroconical. Tip 123 may be coated with a non-stick material, such as polytetrafluoroethylene (a.k.a. PTFE or TEFLON®, manufactured by the E. I. du Pont de Nemours and Company of Wilmington, Del., United States), polyethylene tephthalate (PET), or the like.

In some variations, the antenna assembly 12 includes a distal radiating portion 105 and a proximal radiating portion 140. In some embodiments, a junction member 130 (also referred to herein as a puck) couples the proximal radiating portion 140 and the distal radiating portion 105. In some embodiments, the distal and proximal radiating portions 105, 140 align at the junction member 130, which is generally made of a dielectric material, e.g., adhesives, and are also supported by the inner conductor that extends at least partially through the distal radiating portion 105. Junction member 130, or portions thereof, may be disposed between the proximal and distal radiating portions, 140 and 105. Junction member 130 may be formed from any suitable elastomeric or ceramic dielectric material by any suitable process. In some embodiments, the junction member 130 is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction member 130 may be formed using any suitable overmolding compound by any suitable process, and may include use of a ceramic substrate.

In some embodiments, the antenna assembly 12 may be provided with a coolant chamber (not shown). Additionally, the junction member 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009 (now U.S. Pat. No. 8,118,808), entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

In some embodiments, the antenna assembly 12 may be provided with an outer jacket (not shown) disposed about the distal radiating portion 105, the junction member 130 and/or the proximal radiating portion 140. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition. The outer jacket may be a water cooled catheter formed of a material having low electrical conductivity.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or atop tissue, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few seconds to minutes, to destroy cancerous cells in the target tissue region.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

The length of the antenna for efficient radiation may be dependent on the effective wavelength, $\lambda_{eff}$, which is dependent upon the dielectric properties of the medium being radiated into. Antenna assembly 12 through which microwave energy is transmitted at a wavelength, $\lambda$, may have differing effective wavelengths, $\lambda_{eff}$, depending upon the surrounding medium, e.g., liver tissue, as opposed to breast tissue.

In some embodiments of the probe 100, the first balun structure 108 includes a balun insulator 348 in the form of a substantially cylindrically-shaped, dielectric sleeve coaxially disposed around a distal portion of the feedline 110, and a balun outer conductor 368 in the form of a substantially cylindrically-shaped, electrically-conductive sleeve disposed around the outer peripheral surface of the balun insulator 348. Balun insulator 348 may be formed of any non-conductive insulator, e.g., a TEFLON® sleeve. Balun insulator 348 may be applied by any suitable manner, including, but not limited to, by applying a polymeric coating, and/or by positioning a heat-shrinkable tube (e.g., polyolefin) and raising the temperature thereof to conform the heat shrink tubing to the coaxial feedline 110. Balun outer conductor 368 may be formed of any suitable electrically-conductive material, e.g., metal such as stainless steel, titanium, etc., by any suitable process.

First balun structure 108, according to the embodiment shown in FIG. 3, includes a balun short 378 disposed at the proximal end 106a of the balun insulator 348. Balun short 378 may be formed of any suitable electrically-conductive materials, e.g., copper, gold, silver or other conductive metals or metal alloys. In some embodiments, the balun short 378 has a generally ring-like or truncated tubular shape. Balun short 378 is electrically coupled to the outer conductor 260 of the feedline 110 by any suitable manner of electrical connection, e.g., soldering, welding, or laser welding. Balun short 378 is electrically coupled to the balun outer conductor 368 by any suitable manner of electrical connection.

In some embodiments, the balun outer conductor 368 has a substantially tubular shape, having the proximal end 106a thereof abutting the distal end of the balun short 378, and extending distally from the balun short 378. The distal end 107b of the balun outer conductor 368, according to the embodiment shown in FIG. 3, is positioned substantially adjacent to the distal end 107a of the balun insulator 348. Balun insulator 348 may extend distally beyond the distal end 107b of the balun outer conductor 368, e.g., to enhance microwave performance of the probe 100 and/or provide a desired ablation pattern.

Probe 100, according to embodiments of the present disclosure, includes a second balun structure 129 (also referred to herein as an antenna radiating section air-exposure balun). Second balun structure 129 has a proximal end 127 and a distal end 128. The presently disclosed second balun structure 129 is configured to substantially prevent the propagation of electromagnetic radiation or energy emitted from the antenna assembly 12 proximally, e.g., along the feedline 110, when the probe 100 is energized but not inserted in tissue. FIG. 2 illustrates a diagrammatic representation of a radiation pattern "$R_O$" of electromagnetic energy emitted by the radiating section 50 when the probe 100 is energized but not inserted in tissue, showing that the emitted energy does not propagate along the feedline 110 proximal to the distal end 128 of the second balun structure 129.

Second balun structure 129 may include a balun outer conductor 369 coaxially disposed about the feedline 110 and insulated therefrom along the length of the balun outer conductor 369 by a balun insulator 349, and may include a balun short 379. Antenna radiating section air-exposure balun 129 may be formed similar to, or different than, the first balun structure 108. The shape and size of the first balun structure 108 and the second balun structure 129 may be varied from the configuration depicted in FIG. 3.

As illustrated in FIG. 2, the first balun structure 108 has a distal end 107 that may be positioned at a distance "L1" from the distal end of the antenna assembly 12, and the second balun structure 129 has a distal end 128 that may be positioned at a distance "L2" from the distal end of the antenna assembly 12. In some embodiments, the distance "L1" is about one-half of a wavelength, ½ $\lambda$, in tissue, and the distance "L2" may be about one-half of a wavelength, ½ $\lambda$, in air.

Figure 5:
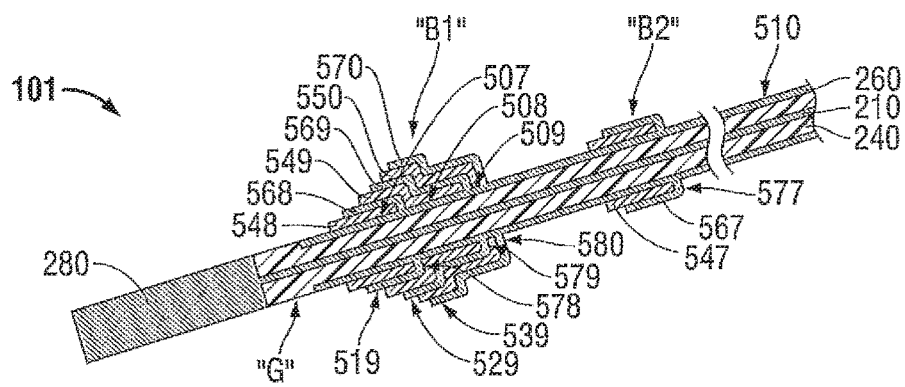
FIG. 5 is a partial, cross-sectional view of another embodiment of an energy applicator in accordance with the present disclosure.

FIG. 5 shows an electromagnetic energy delivery device or probe 101 according to an embodiment of the present disclosure that includes a conductor end portion 280, a feedline 510, a first balun structure "B1" and a second balun structure "B2" (also referred to herein as an antenna radiating section air-exposure balun) disposed proximal to the first balun "B1". Feedline 510 is similar to feedline 110 of FIG. 1 and further description thereof is omitted in the interests of brevity. Conductor end portion 280 may be formed from any suitable electrically conductive material. In some embodiments, the conductor end portion 280 is coupled to an inner conductor 210 and may be formed of the same material as the inner conductor 210. The shape, size and relative positions of the first balun structure "B1" and the second balun structure "B2", which are described below, may be varied from the configuration depicted in FIG. 5. In some embodiments, the distal end of the outer conductor 260 may be spaced apart by a gap "G" from the proximal end of the conductor end portion 280 to define a feed point therebetween.

First balun structure "B1" generally includes a first balun portion 519, a second balun portion 529 and a third balun portion 539. The second balun portion 529 may be disposed so as to at least partially overlap the first balun portion 519, and the third balun portion 539 may be disposed so as to at least partially overlap the second balun portion 529.

First balun portion "B1" includes a balun insulator 548 in the form of a substantially cylindrically-shaped, dielectric sleeve coaxially disposed around a distal portion 507 of the outer conductor 260, and a balun outer conductor 568 in the form of a substantially cylindrically-shaped, electrically-conductive sleeve disposed around the outer peripheral surface of the balun insulator 548, or portion thereof. Balun outer conductor 568 is electrically coupled to the outer conductor 260 at the proximal end 578 of the balun outer conductor 568, e.g., by solder or other suitable electrical connection. Balun insulator 548 may be formed of any suitable insulative material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, metal oxides or other suitable insulator, and may be formed in any suitable manner. Balun outer conductor 568 may be formed of any suitable electrically-conductive materials, e.g., copper, gold, silver or other conductive metals or metal alloys.

Second balun portion 529 includes a balun insulator 549 and a balun outer conductor 569 disposed around the outer peripheral surface of the balun insulator 549, or portion thereof. Balun insulator 549 is disposed around a distal portion 508 of the outer conductor 260, and may overlap at least a proximal portion of the first balun portion 519. Balun outer conductor 569 is electrically coupled to the outer conductor 260 using any suitable electrical connection. In some embodiments, the proximal end 579 of the balun outer conductor 569 may be adapted to allow for connection, e.g., electrically and mechanically, to the outer conductor 260.

Third balun portion 539 includes a balun insulator 550 and a balun outer conductor 570 disposed around the outer peripheral surface of the balun insulator 550, or a portion thereof. Balun insulator 550 is disposed around a distal portion 509 of the outer conductor 260, and may overlap at least a proximal portion of the second balun portion 529. Balun outer conductor 570 is electrically coupled to the outer conductor 260 using any suitable electrical connection. In some embodiments, the proximal end 580 of the balun outer conductor 570 may be adapted to allow for connection, e.g., electrically and mechanically, to the outer conductor 260. The shape, size, spacing, and relative positions of the first balun portion 519, the second balun portion 529, and the third balun portion 539 may be varied from the configuration depicted in FIG. 5.

Antenna radiating section air-exposure balun "B2" may be formed as a nested or overlapping balun (e.g., similar to the first balun structure "B1" shown in FIG. 5). In some embodiments, antenna radiating section air-exposure balun "B2" is a sleeve balun including a balun insulator 547 and a balun outer conductor 567 disposed around the outer peripheral surface of the balun insulator 547, or portion thereof. Balun outer conductor 567 may be formed of any suitable electrically-conductive materials, e.g., copper, gold, silver or other conductive metals or metal alloys. Balun insulator 547 may be formed of any non-conductive insulator, e.g., a TEFLON® sleeve. Balun outer conductor 567 is electrically coupled to the outer conductor 260 at the proximal end 577 of the balun outer conductor 567 by soldering or other means.

Figure 6:
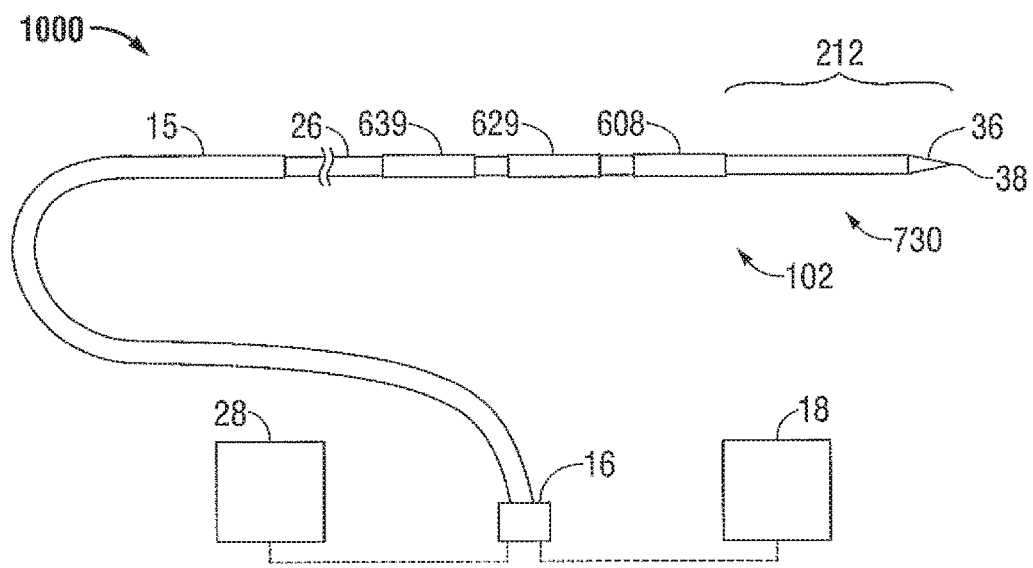
FIG. 6 is a schematic diagram of another embodiment of an ablation system in accordance with the present disclosure.

FIG. 6 shows an electrosurgical system 1000, according to an embodiment of the present disclosure that includes an energy applicator or probe 102. Probe 102 generally includes an antenna assembly 212 having a radiating portion 730 connected by a feedline 26 (or shaft) via a transmission line 15 to a connector 16, which may further operably connect the probe 102 to a power generating source 28, e.g., a microwave or RF electrosurgical generator. Transmission line 15 may provide a conduit (not shown) configured to provide coolant fluid from a coolant source 18 to the probe 102. Feedline 26 generally includes an inner conductor 210, an outer conductor 260, and a dielectric material 240 separating the inner conductor 210 and the outer conductor 260. Feedline 26 is similar to the feedline 110 of FIG. 1 and further description thereof is omitted in the interests of brevity.

In some embodiments, the probe 102 includes a tapered end 36 that terminates in a tip 38 at the distal end of the radiating portion 730. Tapered end 36 allows for insertion of the probe 102 into tissue with minimal resistance. In cases where the radiating portion 730 is inserted into a pre-existing opening, the tip 38 may be rounded or flat.

Figure 7:
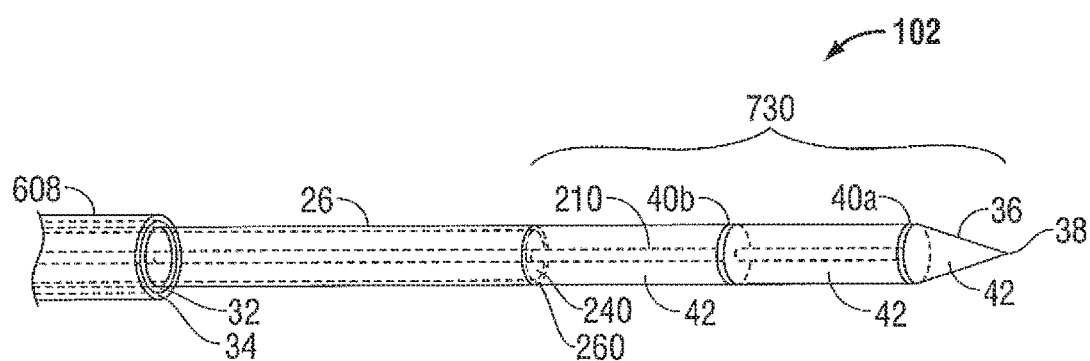
FIG. 7 is a perspective view of a portion of an energy applicator according to another embodiment of the present disclosure.
Figure 8:
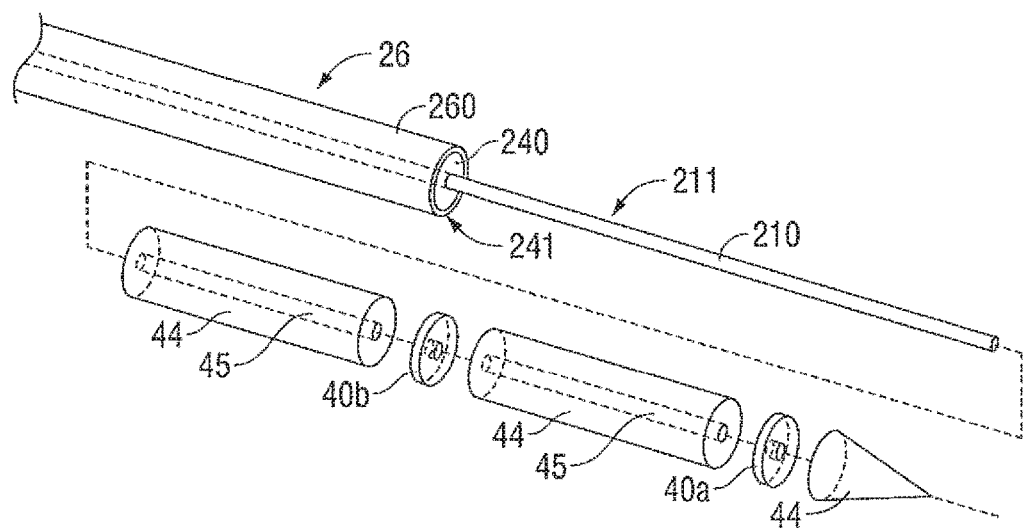
FIG. 8 is a perspective view with parts disassembled of the portion of the energy applicator shown in FIG. 7 according to an embodiment of the present disclosure.
Figure 9:
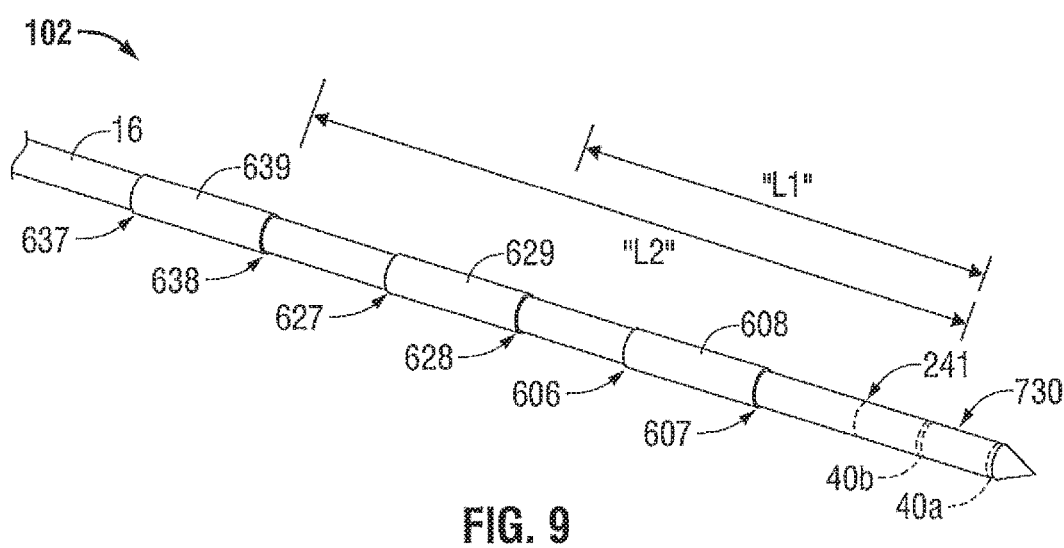
FIG. 9 is a partial, perspective view of an energy applicator according to an embodiment of the present disclosure.

In the embodiment shown in FIGS. 6 through 9, the probe 102 includes a first balun structure 608 disposed around the feedline 26, a second balun structure 629 disposed around the feedline 26 proximal to the first balun structure 629, and a third balun structure 639 disposed around the feedline 26 proximal to the second balun structure 629. As shown in FIG. 9, the first balun structure 608 has a distal end 607 and a proximal end 606. During microwave ablation, when the probe 102 is inserted in tissue, the first balun structure 608 substantially confines microwave energy from the generator 28 to the radiating portion 730 of the probe 102. As shown in FIG. 7, the first balun structure 608 may include an inner dielectric layer 32 and an outer conductive layer 34.

First balun structure 608 may be implemented with a quarter-wave short by using the outer conductive layer 34 around the outer conductor 260 of the feedline 26 separated by the dielectric layer 32. First balun structure 608 is shorted to the outer conductor 260 of the feedline 26 at the proximal end of the first balun structure 608 by soldering or other means. In embodiments, the length of the first balun structure 608 may be from a quarter to a full wavelength. In one embodiment, the dielectric layer 32 is formed from a fluoropolymer such as tetrafluorethylene, perfluorpropylene, or the like, and may have a thickness of about 0.005 inches. The outer conductive layer 34 may be formed from a highly conductive metal, e.g., copper. The shape and size of the first balun structure 608 may be varied from the configuration depicted in FIG. 6.

Inner conductor 210 of the feedline 26 extends distal to the distal end 607 of the first balun structure 608, with the dielectric material 240 and the outer conductor 260 terminating at the proximal end (e.g., 241 shown in FIGS. 8 and 9) of the radiating portion 730. Inner conductor 210 is extruded from the feedline 26 and extends into the radiating portion 730 where the inner conductor 210 is centrally disposed. The extruded portion 211 of the inner conductor 210 may include one or more conductive disks, e.g., a first conductive disk 40a and a second conductive disk 40b, coaxially disposed thereon. First and second conductive disks, 40a and 40b, may be disposed substantially perpendicular to a longitudinal axis defined by the inner conductor 210.

In some embodiments, the first and second conductive disks, 40a and 40b, have a thickness from about 0.01 inches to about 0.02 inches, and may have a diameter from about 0.04 inches to about the thickness of the feedline 26, which in one embodiment is about 0.085 inches. First and second conductive disks, 40a and 40b, may be of different sizes, diameters and thickness. Conductive disks 40, according to embodiments of the present disclosure, are spaced on the inner conductor 210 such that the desired bandwidth is obtained. Conductive disks 40 divide the radiating portion 730 into a number of spaces 42. Examples of radiating portions divided into spaces by conductive disk embodiments are disclosed in commonly assigned U.S. patent application Ser. No. 12/265,024 filed on Nov. 5, 2008 (now U.S. Pat. No. 8,280,525), entitled "DYNAMICALLY MATCHED MICROWAVE ANTENNA FOR TISSUE ABLATION", and U.S. patent application Ser. No. 11/823,639 filed on Jun. 28, 2007, entitled "BROADBAND MICROWAVE APPLICATOR". In some embodiments, the spaces 42 are filled with a dielectric material 44, e.g., to improve the impedance match between the probe 102 and the power generating source 28. In some embodiments, the dielectric material 44 has a dielectric constant of about 2.5 to about 30, and may be made from a ceramic material, such as alumina ceramic, or a plastic material, such as a polyamide plastic (e.g., VESPEL®, available from E. I. du Pont de Nemours and Company of Wilmington, Del., United States). Dielectric material 44 may be configured with a central channel 45 extending longitudinally therethrough to accommodate the inner conductor 210.

As shown in FIG. 9, the second balun structure 629 has a distal end 628 and a proximal end 627, and the third balun structure 639 has a distal end 638 and a proximal end 637. In some embodiments, the distal end 628 of the second balun structure 629 is positioned at a distance "L2" from the second conductive disk 40*b*, and the third balun structure 639 is positioned at a distance "L2" from the second conductive disk 40*b*, as shown in FIG. 9. The distances "L1" and "L2" may be any suitable length and may be measured in fractions of a wavelength. In some embodiments, the distance "L1" is about one-half of a wavelength measured in air and the distance "L2" is about one wavelength measured in air.

In some embodiments, the distal end 628 of the second balun structure 629 and/or the distal end 638 of the third balun structure 639 may be positioned at a distance that is a fraction of a wavelength (e.g., measured in air) from the first conductive disk 40*a*. In some embodiments, the distal end 628 of the second balun structure 629 and/or the distal end 638 of the third balun structure 639 may be positioned at a distance that is a fraction of a wavelength (e.g., measured in air) from the proximal end 241 of the radiating portion 730.

Embodiments of the second balun structure 629 and/or the third balun structure 639, according to the present disclosure, may be manually or automatically movable structures that selectably allow positioning thereof at a range of positions along the feedline 26. Probe 102, according to embodiments, may be configured to provide automatically adjustable positioning of the second balun structure 629 and/or the third balun structure 639 at various positions relative to a suitable reference position on the probe 102. Examples of reference positions that may be suitable include the location of the first conductive disk 40*a*, the location of the second conductive disk 40*b*, the distal end of the radiating portion 730, and the proximal end 241 of the radiating portion 730.

Figure 10:
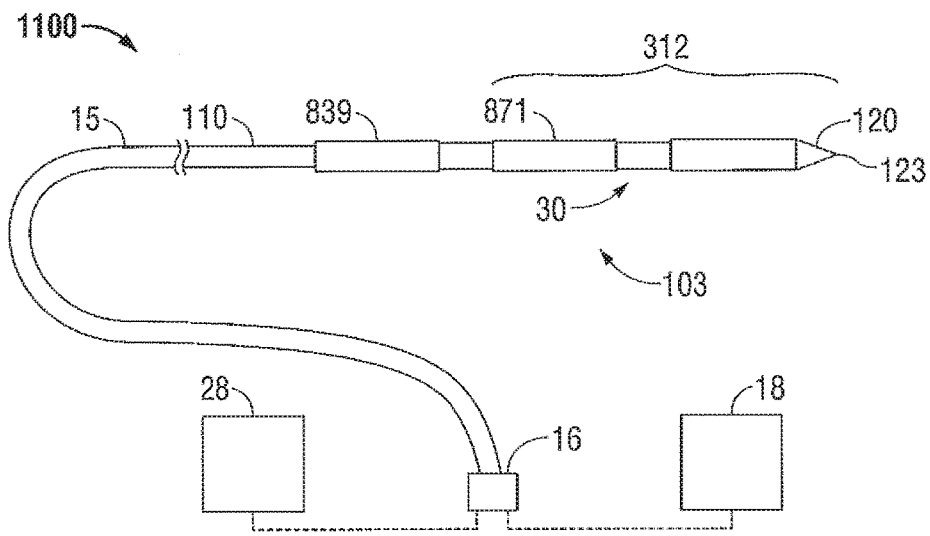
FIG. 10 is a schematic diagram of yet another embodiment of an ablation system in accordance with the present disclosure.
Figure 22:
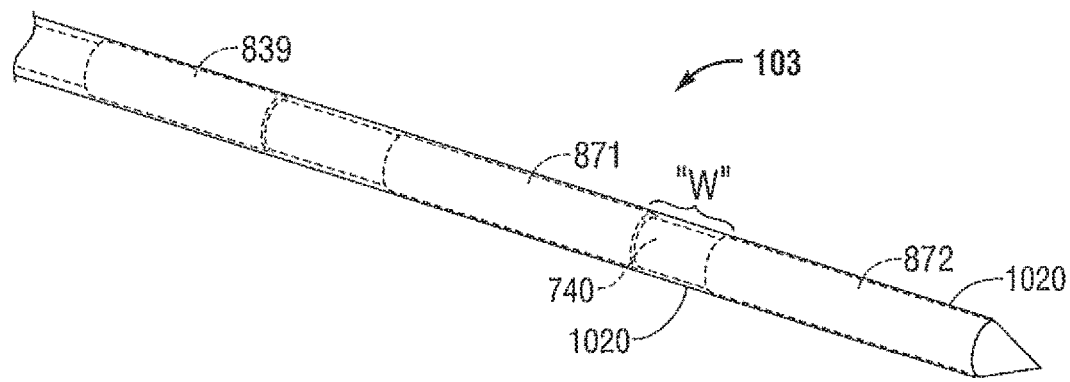
FIG. 22 is a partial, perspective view of the energy applicator of FIG. 21 shown with a layer disposed along the length of the elongated shaft and overlying the proximal and distal electrically-conductive sleeve members and the radiating section air-exposure balun and bridging the gaps therebetween according to an embodiment of the present disclosure.
Figure 23:
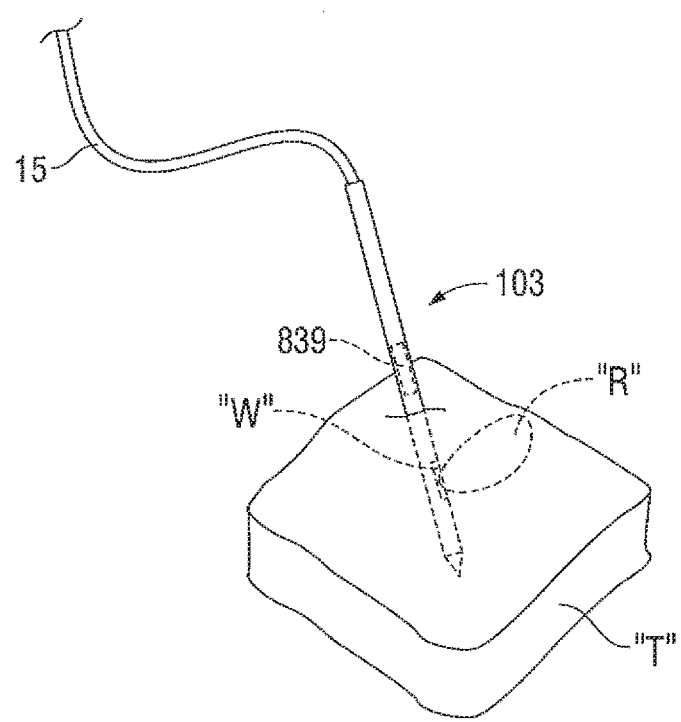
FIG. 23 is a diagrammatic representation of a radiation pattern of electromagnetic energy delivered into tissue by an energy applicator, such as the energy applicator of FIG. 11, according to an embodiment of the present disclosure.

FIG. 10 shows an electrosurgical system 1100 according to an embodiment of the present disclosure that includes an energy applicator or probe 103 with a directional radiation pattern (e.g., "R" shown in FIG. 23). Probe 103 generally includes an antenna assembly 312 having a radiating portion 30 connected by a feedline 110 (or shaft) via a transmission line 15 to a connector 16, which may further operably connect the probe 103 to a power generating source 28, e.g., a microwave or RF electrosurgical generator. Located at the distal end of the antenna assembly 312 is an end cap or tapered portion 120, which may terminate in a sharp tip 123 to allow for insertion into tissue with minimal resistance. An embodiment of an energy applicator with a directional radiation pattern suitable for use in tissue ablation applications, such as the probe 103 of FIG. 10, in accordance with the present disclosure, is shown in more detail in FIGS. 11 through 22.

FIGS. 11 through 22 show a sequentially-illustrated, assembly of components forming an energy applicator or probe 103 having a dielectric loaded coaxial aperture (e.g., "W" shown in FIG. 22) with distally positioned resonant structure (e.g., 909 shown in FIG. 18) in accordance with the present disclosure. As shown in FIGS. 21 through 23, embodiments of an energy applicator with a directional radiation pattern in accordance with the present disclosure may include a radiating section air-exposure balun 839.

According to an embodiment of the present disclosure, an energy applicator segment or probe (shown generally as 20 in FIGS. 11 and 12) is provided with a coaxial feedline 226 having an inner conductor 220 that extends along the longitudinal axis "A" of the energy applicator segment 200, an outer conductor 224 coaxially disposed about the inner conductor 220, and a dielectric material 222 disposed therebetween. In some embodiments, the inner conductor 220 has a diameter "D1" and the dielectric material 222 has an outer diameter "D2".

At the distal end of the feedline 226, a portion of the dielectric material 222 may extend beyond the outer conductor 224. Additionally, or alternatively, a portion of the inner conductor 220 (e.g., 22 shown in FIG. 11) may extend beyond the dielectric material 222 and the outer conductor 224. In some embodiments, the antenna assembly 312, or portions thereof, may be coupled to the inner conductor portion 22. Alternatively, the antenna assembly 312, or portions thereof, may be coupled to an elongated conductor (e.g., similar to the inner conductor portion 22), wherein the elongated conductor is electrically coupled to the inner conductor 220 of the feedline 226.

Figure 11:
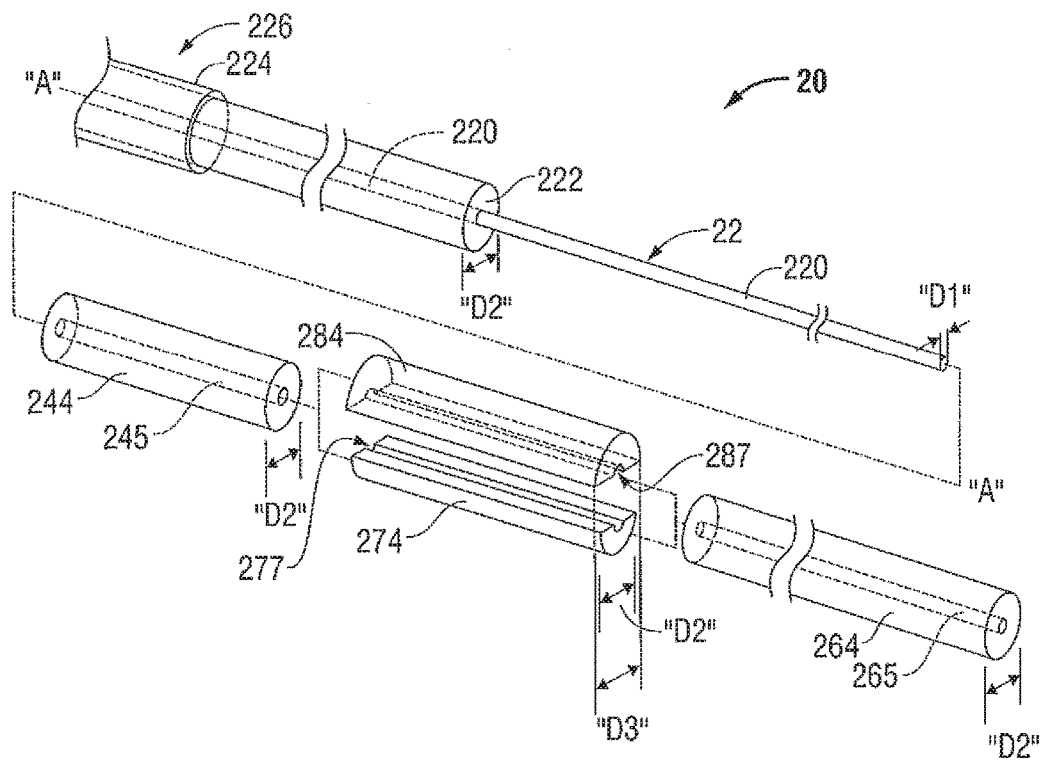
FIG. 11 is a perspective view with parts disassembled of a portion of an energy applicator according to an embodiment of the present disclosure.
Figure 12:
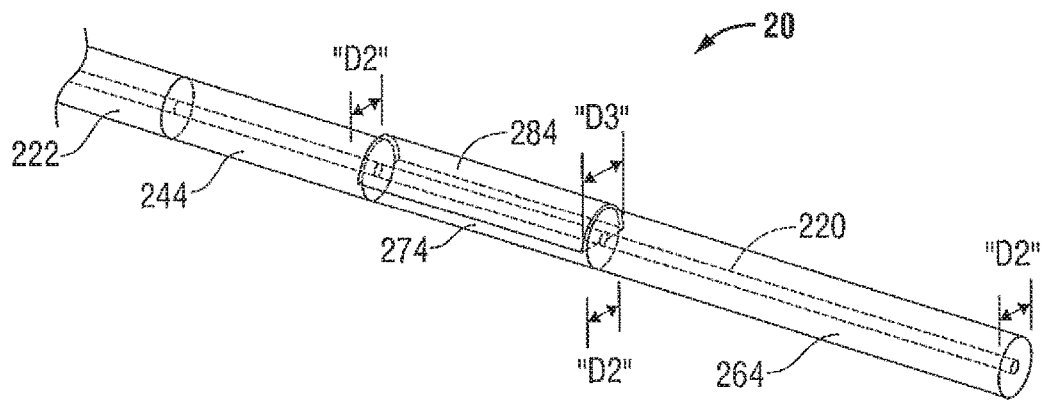
FIG. 12 is a perspective assembled view of the portion of the energy applicator shown in FIG. 11 according to an embodiment of the present disclosure.

As shown in FIGS. 11 and 12, a proximal cylindrical dielectric sleeve 244 may be coupled to the inner conductor 220 at a distal end of the coaxial feedline 226. Additionally, or alternatively, a first dielectric segment 284 and a second dielectric segment 274 may be coupled to the inner conductor 220. Additionally, or alternatively, a distal cylindrical dielectric sleeve 264 may be coupled to the inner conductor 220.

Proximal cylindrical dielectric sleeve 244, first dielectric segment 284 and a second dielectric segment 274 may be formed from dielectric materials that provide an impedance match from the coaxial feedline 226. First dielectric segment 284 may be formed from a material with a dielectric constant that is higher than the dielectric constant of the second dielectric segment 274, e.g., to maximize energy radiated into the surrounding medium, e.g., tissue.

In some embodiments, a proximal cylindrical dielectric sleeve 244, having a diameter "D2", is coupled to the inner conductor 220. Proximal cylindrical dielectric sleeve 244 may be configured with a central channel 245 extending longitudinally therethrough to accommodate the inner conductor 220. Proximal cylindrical dielectric sleeve 244 may be formed from any suitable dielectric material. In some embodiments, the proximal cylindrical dielectric sleeve 244 is formed from a material with a dielectric constant in the range of about 2 to about 10.

In some embodiments, a distal cylindrical dielectric sleeve 264, having a diameter "D2", is coupled to the inner conductor 220. Distal cylindrical dielectric sleeve 264 may be formed from any suitable dielectric material. Distal cylindrical dielectric sleeve 264 may be disposed distally of the proximal cylindrical dielectric sleeve 244 and may be configured with a central channel 265 extending longitudinally therethrough to accommodate the inner conductor 220. In some embodiments, the distal cylindrical dielectric sleeve 264 is formed from a material with a dielectric constant different than the dielectric constant of the proximal cylindrical dielectric sleeve 244. Distal cylindrical dielectric sleeve 264 may be a high dielectric material, e.g., a material with a dielectric constant in the range of about 3 to about 50, to shorten the effective wavelength, $\lambda_{\mathit{eff}}$, of energy.

Figure 13:
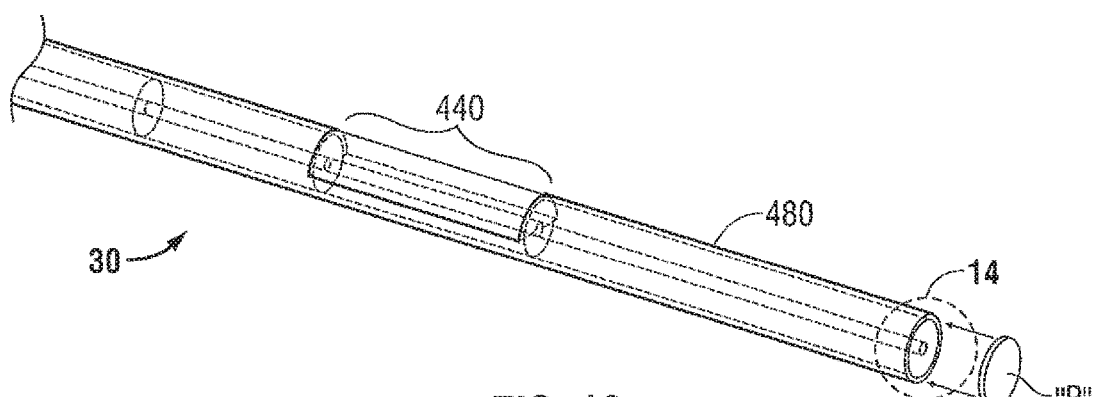
FIG. 13 is a perspective, partly separated view of the portion of the energy applicator of FIG. 12 provided with an elongated shaft having an opening therethrough and an end cap according to an embodiment of the present disclosure.
Figure 14:
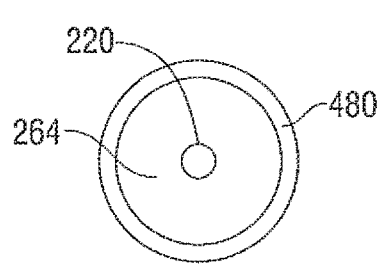
FIG. 14 is an enlarged view of the indicated area of detail of FIG. 13 according to an embodiment of the present disclosure.
Figure 15:
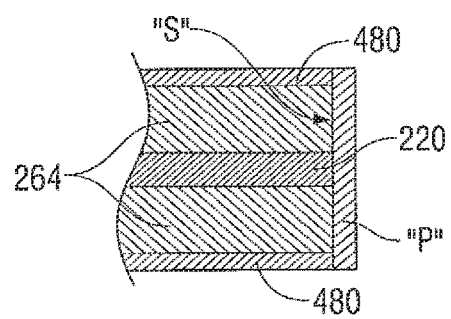
FIG. 15 is a partial, cross-sectional view of the energy applicator of FIG. 13 according to an embodiment of the present disclosure.

The length of the distal cylindrical dielectric sleeve 264 may be varied, depending on the dielectric constant of the material selected, to allow positioning of a radiating aperture (e.g., "W" shown in FIGS. 22 and 23) at a quarter wavelength (or half wavelength, etc.) from a distal short (e.g., "P" shown in FIGS. 13 and 15). For example, the physical length of the distal cylindrical dielectric sleeve 264 for a selected dielectric constant to allow positioning of an aperture at a selected wavelength from a distal short may be calculated using Equation 1.

$$\lambda = \frac{c}{f\sqrt{\varepsilon_r}}, \qquad (1)$$

where c is the speed of light, f is the frequency, and $\varepsilon_r$ is the dielectric constant. For example, in a case where an aperture is to be positioned at a quarter wavelength, given a dielectric sleeve having a dielectric constant $\varepsilon_r$, using Equation 1, the length l of the dielectric sleeve is calculated as:

$$l = \frac{\lambda}{4} = \frac{c}{4f\sqrt{\varepsilon_r}}.$$

In some embodiments, a first dielectric segment 284 and a second dielectric segment 274 are coupled to the inner conductor 220. As shown in FIGS. 11 and 12, the first and second dielectric segments 284, 274 may be disposed between the proximal cylindrical dielectric sleeve 244 and the distal cylindrical dielectric sleeve 264. First and second dielectric segments 284, 274 generally include one or more flat planar surfaces and a partial cylindrical surface. The shape and size of the first and second dielectric segments 284, 274 may be varied from the configuration depicted in FIGS. 11-13. In some embodiments, the first dielectric segment 284 is formed from a material with a dielectric constant in the range of about 2 to about 30. In some embodiments, the second dielectric segment 274 is formed from a material with a dielectric constant in the range of about 2 to about 30.

In some embodiments, the first dielectric segment 284 has a substantially half-cylindrical shape, having a diameter "D3", and includes a flat planar surface configured with a recess in the form of a groove 287 extending longitudinally across the flat planar surface. In some embodiments, the second dielectric segment 274 has a substantially half-cylindrical shape, having a diameter "D2", and includes a flat planar surface configured with a recess in the form of a groove 277 extending longitudinally across the flat planar surface. Grooves 287 and 277 may be configured to accommodate a portion of the inner conductor 220. In some embodiments, when the first and second dielectric segments 284, 274 are coupled to the inner conductor 220, the respective flat planar surfaces of the first and second dielectric segments 284, 274 contact one another. The shape and size of the grooves 287 and 277 may be varied from the configuration depicted in FIG. 11.

FIGS. 13 through 16 show an energy applicator segment 30 according to an embodiment of the present disclosure that is similar to the energy applicator segment 20 of FIG. 11, except for an elongated shaft 480 (outlined in bold lines in FIG. 13) having an opening 440 therethrough, and an end cap "P" disposed distally to the distal end of the elongated shaft 480. In some embodiments, the elongated shaft 480 has an inner diameter "D2" and an outer diameter "D3". As shown in FIG. 13, the end cap "P" may have a disc- or plate-like shape. End cap "P" may be formed of any suitable electrically-conductive material, e.g., metal such as stainless steel, titanium, etc. As shown in FIG. 15, the proximal surface "S" of the end cap "P" makes contact with both the distal end of the inner conductor 220 and the distal end of the elongated shaft 480, thereby forming a distal short. The shape and size of the end cap "P" may be varied from the configuration depicted in FIGS. 13 and 15.

Figure 16:
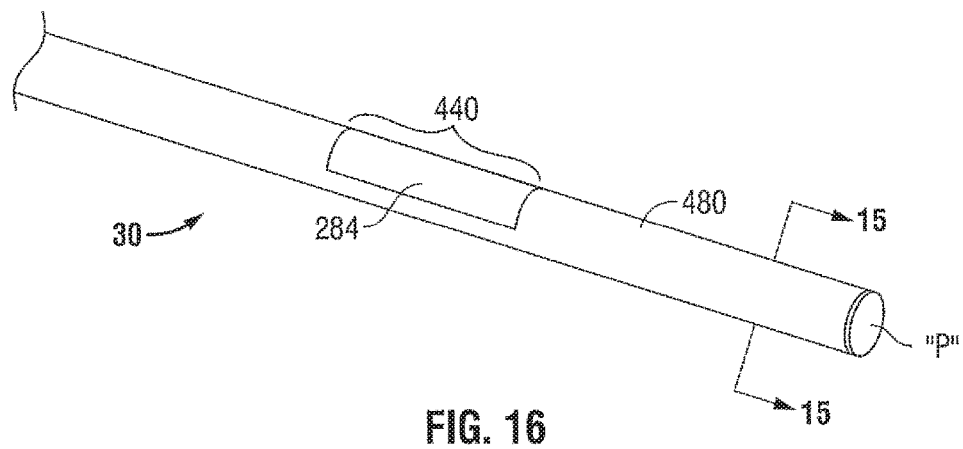
FIG. 16 is a perspective, assembled view of the portion of the energy applicator of FIG. 13 according to an embodiment of the present disclosure.

As shown in FIG. 16, the opening 440 in the elongated shaft 480 may be aligned with the first dielectric segment 284. In some embodiments, the first dielectric segment 284 and the elongated shaft 480 may be substantially concentric to a longitudinal axis (e.g., "A"-"A" shown in FIG. 11) of the energy applicator. Elongated shaft 480 may be electrically coupled to the outer conductor 224 of the coaxial feedline 226.

Opening 440 is made by removing a radial portion the elongated shaft 480 an optimized length back from the distal short. In some embodiments, the opening 440 is positioned to maximize directivity and coupling of microwave energy into tissue, e.g., opening 440 may be placed at the voltage maximum of the standing wave created by the shorted coaxial distal end. Opening 440 may be of any length and radial angle to achieve the desired amount of coax to free space coupling and radiation directivity.

The dielectric constant of dielectric materials on either side of the opening 440, proximal or distal, may vary with distance from the opening 440 to achieve impedance match and optimal energy delivery and directivity to tissue. The dielectric materials filling the coaxial structure at the site of the opening 440 may vary in dielectric constant with shells or more complex dielectric layering to achieve the optimum antenna directivity and energy to tissue delivery.

In some embodiments, the first dielectric segment 284 has a diameter "D2" and the elongated shaft 480 has an outer diameter "D3", where "D3" is larger than "D2". In such cases, the opening 440 may be filled with a nonconductive radio frequency transparent material, e.g., a glass fiber epoxy composite or polyimide. This may be accomplished in an over molding process. The window may also be created by placing a heat shrink or rigid composite sleeve along the entire antenna assembly. Examples of dielectric material configurations at the site of a window or opening in an energy applicator are disclosed in commonly assigned U.S. patent application Ser. No. 12/535,851 filed on Aug. 5, 2009 (now U.S. Pat. No. 8,328,799), entitled "ELECTROSURGICAL DEVICES HAVING DIELECTRIC LOADED COAXIAL APERTURE WITH DISTALLY POSITIONED RESONANT STRUCTURE AND METHOD OF MANUFACTURING SAME".

Figure 17:
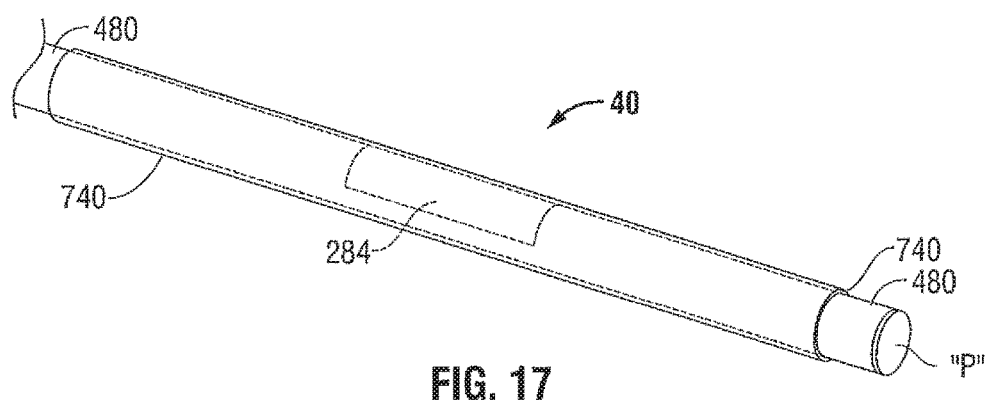
FIG. 17 is a partial, perspective view of the energy applicator of FIG. 16 shown with a dielectric sleeve member surrounding a portion of the elongated shaft including the opening in the elongated shaft, according to an embodiment of the present disclosure.

FIG. 17 shows an energy applicator segment 40 according to an embodiment of the present disclosure that is similar to the energy applicator segment 30 of FIG. 16, except for a dielectric sleeve member 740 (also referred to herein as a balun insulator) disposed coaxially about a portion of the elongated shaft 480. Balun insulator 740 may be formed of any non-conductive insulator, e.g., a TEFLON® sleeve. Balun insulator 740 may extend fully or partially over the opening 440 in the elongated shaft. In some embodiments, the balun insulator 740 extends fully over the opening 440 and the half-cylindrical dielectric member 284 disposed therein. The shape, size, and arrangement of the dielectric balun insulator 740 (e.g., its position relative to the opening 440 and/or the end cap "P") may be varied from the configuration depicted in FIG. 17. Balun insulator 740 may extend beyond the open ends of one or more electrically-conductive sleeve members (e.g., 871 and 872 shown in FIG. 18) of a balun structure (e.g., 909 shown in FIG. 18) to enhance effectiveness of the balun.

Figure 18:
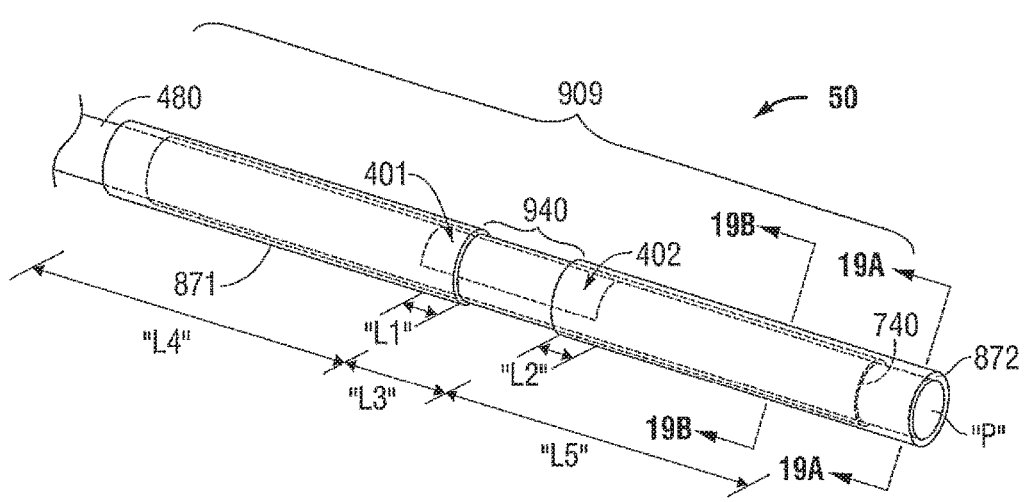
FIG. 18 is a partial, perspective view of the energy applicator of FIG. 17 shown with portions of the dielectric sleeve member and the opening in the elongated shaft (in phantom lines) surrounded by axially aligned proximal and distal electrically-conductive sleeve members having a gap therebetween according to an embodiment of the present disclosure.

FIG. 18 shows an energy applicator segment 50 according to an embodiment of the present disclosure that is similar to the energy applicator segment 40 of FIG. 17, except for a first electrically-conductive sleeve member 871 and a second electrically-conductive sleeve member 872 (also referred to herein as balun outer conductors) axially aligned with a gap 940 therebetween. A proximal end portion of the first electrically-conductive sleeve member 871 may be coupled to a proximal portion of the elongated shaft 480. A distal end portion of the second electrically-conductive sleeve member 872 may be coupled to a distal portion of the elongated shaft 480, e.g., as shown in FIG. 19A. First and second electrically-conductive sleeve members 871, 872 may be formed of any suitable electrically-conductive material, e.g., metal such as stainless steel, aluminum, titanium, copper, etc.

First and second electrically-conductive sleeve members 871, 872 may overlap portions of the window 440 in the elongated shaft 480. As shown in FIG. 18, the first electrically-conductive sleeve member 871 may overlap a proximal portion 401, having a length "L1", of the window 440, and the second electrically-conductive sleeve member 872 may overlap a distal portion 402, having a length "L2", of the window 440, whereby a gap 940, having a length "L3", is formed therebetween. In some embodiments, the first electrically-conductive sleeve member 871 has a length "L4", wherein "L4" may be a quarter wavelength or a half wavelength. In some embodiments, the second electrically-conductive sleeve member 872 has a length "L5", wherein "L5" may be a quarter wavelength or a half wavelength. First and second electrically-conductive sleeve members 871, 872 may have any suitable length.

FIG. 20 shows an energy applicator segment 60 according to an embodiment of the present disclosure that is similar to the energy applicator segment 50 of FIG. 18, except for a tapered portion 920 extending distally from the distal end cap "P". Tapered portion 920 may terminate in a sharp tip 923 to allow for insertion into tissue with minimal resistance. In those cases where the energy applicator segment 60 is inserted into a pre-existing opening, the tip 923 may be rounded or flat. The shape and size of the tapered portion 920 may be varied from the configuration depicted in FIG. 20.

FIG. 21 shows an energy applicator segment 70 according to an embodiment of the present disclosure that is similar to the energy applicator segment 60 of FIG. 20, except for a radiating section air-exposure balun disposed proximal to the first and second electrically-conductive sleeve members 871, 872 of the distally positioned resonant structure (e.g., 909 shown in FIG. 18).

FIG. 22 shows an embodiment of an energy applicator 103 in accordance with the present disclosure. As shown in FIG. 22, an outer jacket 1020 may be provided to the energy applicator segment 70 of FIG. 21. In some embodiments, the outer jacket 1020 is made of an insulating material, such as, for example, a polyimide or similar dielectric material. Outer jacket 1020 may be a water-cooled catheter formed of a material having low electrical conductivity. The outer surface of the outer jacket 1020 may be coated with a suitable lubricious substance, such as TEFLON®, to aid in the movement of the outer jacket 1020 in or through tissue as well as to aid in preventing tissue from sticking thereto.

FIG. 23 shows an embodiment of an energy applicator (e.g., 103 shown in FIG. 22) coupled to a transmission line 15 according to the present disclosure. Transmission line 15 may connect the energy applicator 103 to a power generating source, e.g., a microwave or RF electrosurgical generator. During a procedure, e.g., an ablation procedure, the energy applicator 103 is inserted into or placed adjacent to tissue "T" and energy is supplied thereto. Energy applicator 103 may be placed percutaneously or atop tissue. Ultrasound or computed tomography (CT) guidance may be used to accurately guide the energy applicator 103 into the area of tissue "T" to be treated.

Energy applicator 103 may be rotatable about a longitudinal axis "A-A" (shown in FIG. 11) such that the directional radiation pattern "R" rotates therewith. Examples of antenna assemblies rotatable about axis "A-A" such that any elongated radiation lobes rotates therewith are disclosed in commonly assigned U.S. patent application Ser. No. 12/197,405 filed on Aug. 25, 2008 (now U.S. Pat. No. 8,211,098), entitled "MICROWAVE ANTENNA ASSEMBLY HAVING A DIELECTRIC BODY PORTION WITH RADIAL PARTITIONS OF DIELECTRIC MATERIAL".

Energy applicator 103 may include an indicia alignment mark (not shown) such as a colored strip or the like (e.g., to provide a visual cue to the surgeon to allow orientation of the direction of flow of the energy to coincide with the indicia alignment mark) and/or indicia graduation marks (not shown) for insertion depth reference (e.g., to indicate the position of the opening "W" relative to the surface of the tissue "T"). Examples of indicia alignment mark and the indicia graduation mark embodiments are disclosed in commonly assigned U.S. patent application Ser. No. 12/476,960 filed on Jun. 2, 2009 (now U.S. Pat. No. 8,235,981), entitled "ELECTROSURGICAL DEVICES WITH DIRECTIONAL RADIATION PATTERN".

Figure 24:
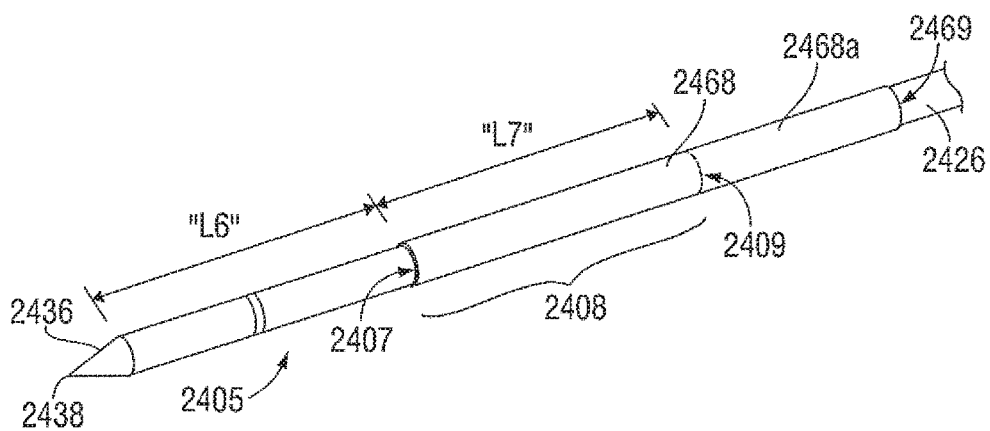
FIG. 24 is a partial, perspective view of an energy applicator according to another embodiment of the present disclosure.
Figure 25:
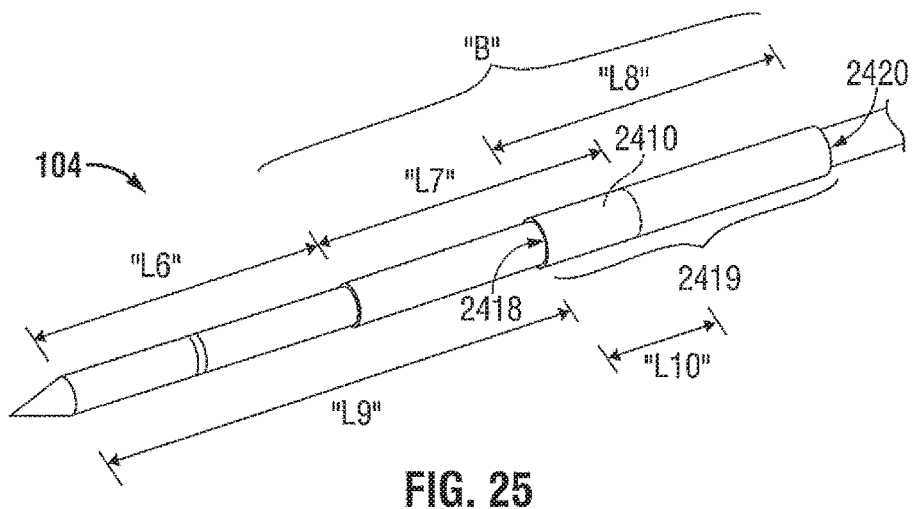
FIG. 25 is a partial, perspective view of the energy applicator of FIG. 24 shown with a radiating section air-exposure balun according to an embodiment of the present disclosure.
Figure 26:
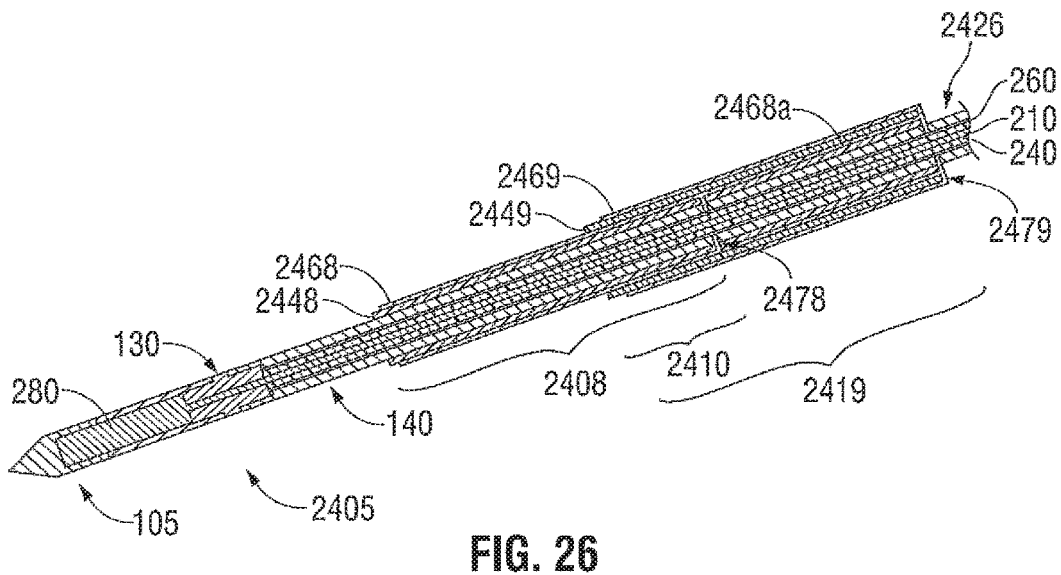
FIG. 26 is a partial, cross-sectional view of the energy applicator of FIG. 25 according to an embodiment of the present disclosure.

FIGS. 24 and 25 show a sequentially-illustrated, assembly of components forming an energy applicator or probe 104 according to an embodiment of the present disclosure that includes an overlapping balun structure "B". FIG. 26 shows a cross-sectional view of the probe 104 including the balun structure "B" according to an embodiment of the present disclosure.

Probe 104 generally includes a feedline 2426 having an inner conductor 210, an outer conductor 260, and a dielectric material 240 disposed therebetween, and a radiating section 2405 operably coupled to the feedline 2426. In some embodiments, the probe 104 includes a tapered end 2436 that terminates in a tip 2438 at the distal end of the radiating portion 2405. Tapered end 2436 allows for insertion of the probe 104 into tissue with minimal resistance. In cases where the radiating portion 2405 is inserted into a pre-existing opening, the tip 2438 may be rounded or flat.

As shown in FIG. 26, the radiating section 2405 of the probe 104 includes a conductor end portion 280 that is formed from any suitable electrically conductive material. Conductor end portion 280 is electrically coupled to the inner conductor 210, and may have any suitable length. Probe 104 may include a distal radiating portion 105 and a proximal radiating portion 140. In some embodiments, a junction member 130 couples the proximal radiating portion 140 and the distal radiating portion 105. Conductor end portion 280 and the junction member 130 shown in FIG. 26 are similar to the like-numbered conductor end portion and junction member of FIG. 3 and further description thereof is omitted in the interests of brevity.

Balun structure "B" generally includes a first balun structure 2408 disposed proximal to the radiating section 2405, and a second balun structure 2419 (also referred to herein as an antenna radiating section air-exposure balun) overlapping a proximal portion 2410 of the first balun structure 2408. The presently-disclosed balun structure "B" is configured to substantially prevent the propagation of energy emitted from the radiating section 2405 of the probe 104 proximally, e.g., along the feedline 2426, when the probe 104 is energized but not disposed in tissue.

First balun structure 2408 includes a distal end 2407 and a proximal end 2409, and the antenna radiating section air-exposure balun 2419 including a distal end 2418 and a proximal end 2420. First balun structure 2408 may have any suitable length "L7", and the antenna radiating section air-exposure balun 2419 may have any suitable length "L8". As cooperatively shown in FIGS. 24 and 25, the antenna radiating section air-exposure balun 2419 overlaps the first balun structure 2408 by a length "L10". The shape, size, spacing, and relative positions of the first balun structure 2408 and the second balun structure 2419 (e.g., in relation to the distal end of the radiating section 2405) may be varied from the configuration depicted in FIGS. 24 and 25.

First balun structure 2408 may include a balun outer conductor 2468 (e.g., similar to the balun outer conductor 368 of the first balun structure 108 of FIG. 3) coaxially disposed about a balun insulator 2448 (e.g., similar to the balun insulator 348 of FIG. 3), or portions thereof. Balun insulator 2448 may extend distally beyond the distal end of the balun outer conductor 2468, e.g., to enhance microwave performance of the probe 104 and/or provide a desired ablation pattern. In some embodiments, the balun outer conductor 2468 may include a segment 2468a that extends proximal to the proximal end 2409 of the first balun structure 2408. Balun outer conductor segment 2468a according to embodiments of the present disclosure forms a smooth inner conductor layer for the antenna radiating section air-exposure balun 2419.

First balun structure 2408, according to the embodiment shown in FIG. 26, includes a balun short 2478 disposed at the proximal end of the balun insulator 2448. Balun short 2478 may be formed of any suitable electrically-conductive materials, e.g., copper, gold, silver or other conductive metals or metal alloys. In some embodiments, the balun short 2478 has a generally ring-like or truncated tubular shape. Balun short 2478 is electrically coupled to the outer conductor 260 of the feedline 2426 by any suitable manner of electrical connection, e.g., soldering, welding, or laser welding. Balun short 2478 is electrically coupled to the balun outer conductor 2468 by any suitable manner of electrical connection.

Antenna radiating section air-exposure balun 2419 includes a balun insulator 2449 coaxially disposed about a proximal portion 2410 of the first balun structure 2408. Balun insulator 2449 may extend to the proximal end 2469 of the balun outer conductor segment 2468a. Balun insulator 2449 may be formed of any non-conductive insulator, e.g., a Teflon® sleeve, and may be applied by any suitable manner. A balun outer conductor 2469 is coaxially disposed about the balun insulator 2449, or portions thereof. Balun outer conductor 2469 is electrically coupled to the outer conductor 260 using any suitable electrical connection. In some embodiments, the proximal end 2479 of the balun outer conductor 2469 may be adapted to allow for connection, e.g., electrically and mechanically, to the outer conductor 260.

In some embodiments, when the probe 104 is energized in tissue, the radiating section 2405 has a length "L6", e.g., ½ λ (in tissue), and when the energy applicator 104 is energized but not disposed in tissue, the radiating section has a length "L9", e.g., ½ λ (in air).

Hereinafter, a method of directing energy to tissue, in accordance with the present disclosure, is described with reference to FIG. 27. It is to be understood that the steps of the method provided herein may be performed in combination and in a different order than presented herein without departing from the scope of the disclosure.

Figure 27:
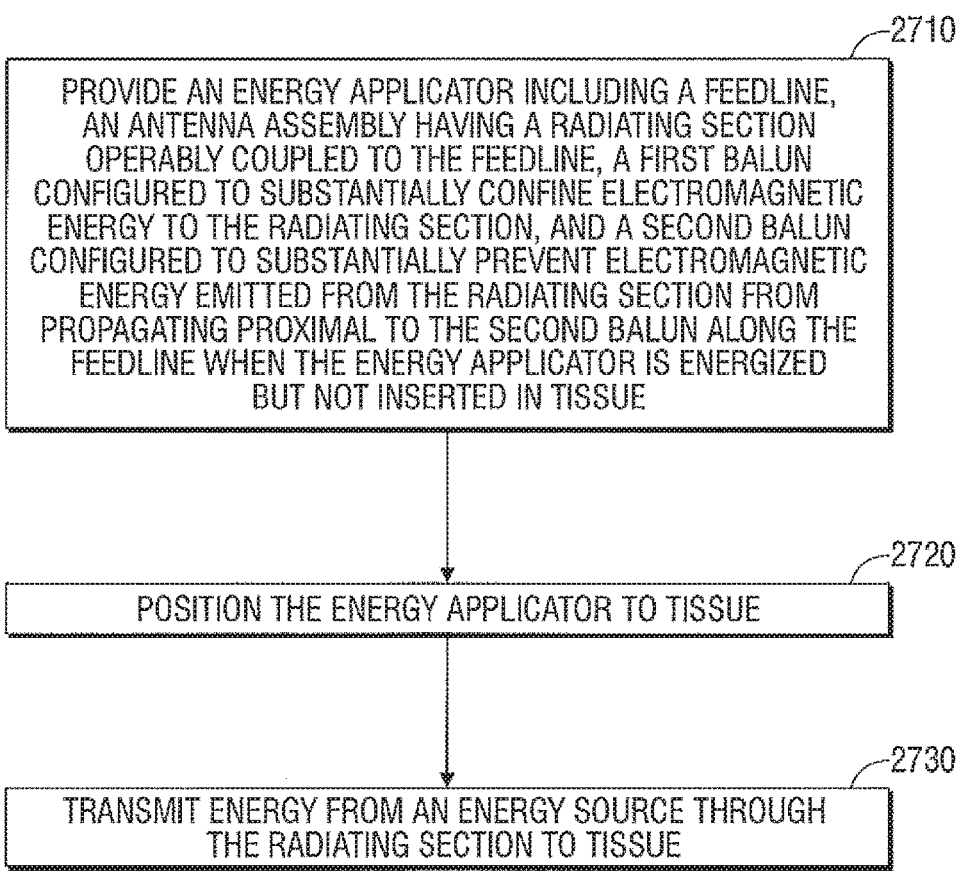
FIG. 27 is a flowchart illustrating a method of directing energy to tissue according to an embodiment of the present disclosure.

FIG. 27 is a flowchart illustrating a method of directing energy to tissue according to an embodiment of the present disclosure. In step 2710, an energy applicator (e.g., 100 shown in FIG. 1) is provided. The energy applicator includes a feedline (e.g., 110 shown in FIG. 1) having an inner conductor (e.g., 210 shown in FIG. 3), an outer conductor (e.g., 260 shown in FIG. 3), and a dielectric material (e.g., 240 shown in FIG. 3) disposed therebetween, and an antenna assembly (e.g., 12 shown in FIG. 1) having a radiating section (e.g., 50 shown in FIG. 2) operably coupled to the feedline.

The energy applicator (e.g., 100 shown in FIG. 1) also includes a first balun (e.g., 108 shown in FIG. 1) configured to substantially confine energy to the radiating section, and a second balun (e.g., 129 shown in FIG. 1) configured to substantially prevent energy emitted from the radiating section from propagating proximal to the second balun along the feedline when the energy applicator is energized but not inserted in tissue. The first balun structure may be a quarter-wave sleeve balun.

In step 2720, the energy applicator (e.g., 100 shown in FIG. 1) is positioned to tissue. The energy applicator may be inserted directly into tissue (e.g., "T" shown in FIG. 24), inserted through a lumen, e.g., a vein, needle, endoscope or catheter, placed into the body during surgery by a clinician, or positioned in the body by other suitable methods known in the art. The energy applicator may be configured to operate with a directional radiation pattern.

In step 2730, energy is transmitted from an energy source (e.g., 28 shown in FIG. 1) through the radiating section (e.g., 50 shown in FIG. 2) to tissue. The energy source may be any suitable electrosurgical generator for generating an output signal. In some embodiments, the energy source is a microwave energy source, and may be configured to provide microwave energy at an operational frequency from about 300 MHz to about 10 GHz.

The above-described electrosurgical devices including embodiments of a radiating section air-exposure balun in accordance with the present disclosure for treating tissue and methods of directing electromagnetic radiation to a target volume of tissue may help protect a user against health risks associated with radiation exposure, e.g., by limiting and/or reducing the user's risk of exposure to radiation when the probe is energized but not inserted in tissue.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An energy applicator for directing energy to tissue, comprising:
   a feedline having an outer conductor;
   a radiating section operably coupled to the feedline;
   a first balun portion including:
      a first balun insulator disposed around the outer conductor of the feedline; and
      a first balun outer conductor disposed around the first balun insulator, the first balun outer conductor including:
         a balun short disposed adjacent a proximal portion of the first balun insulator and electrically coupled the outer conductor of the feedline; and
         a segment extending proximally relative to the balun short, the segment electrically coupled to the outer conductor of the feedline at a location proximal of the balun short; and
   a second balun portion including:
      a second balun insulator disposed around the segment of the first balun outer conductor; and
      a second balun outer conductor disposed around the second balun insulator.

2. The energy applicator according to claim 1, wherein the first balun insulator terminates distally of the balun short of the first balun outer conductor.

3. The energy applicator according to claim 1, wherein at least one of the second balun insulator or the second balun outer conductor extends proximally of the balun short of the first balun outer conductor.

4. The energy applicator according to claim 1, wherein the second balun outer conductor has a proximal portion electrically coupled to the outer conductor of the feedline.

5. The energy applicator according to claim 4, wherein the proximal portion of the second balun outer conductor is in contact with the segment of the first balun outer conductor.

6. The energy applicator according to claim 1, wherein the first balun insulator extends distally beyond a distal-most end of the first balun outer conductor.

7. The energy applicator according to claim 6, wherein the second balun insulator extends distally beyond a distal-most end of the second balun outer conductor.

8. The energy applicator according to claim 1, wherein the first balun outer conductor is in direct contact with the first balun insulator.

9. The energy applicator according to claim 1, wherein the balun short of the first balun outer conductor has a truncated tubular shape.

10. The energy applicator according to claim 1, wherein the second balun portion extends both proximally and distally of the balun short of the first balun outer conductor.

* * * * *